United States Patent [19]

Loev et al.

[11] Patent Number: 4,619,945
[45] Date of Patent: Oct. 28, 1986

[54] POLYENE COMPOUNDS USEFUL IN THE TREATMENT OF ALLERGIC RESPONSES

[75] Inventors: Bernard Loev, Scarsdale; Wan-Kit Chan, Yorktown Heights, both of N.Y.

[73] Assignee: USV Pharmaceutical Corp, Tuckahoe, N.Y.

[21] Appl. No.: 785,682

[22] Filed: Oct. 9, 1985

[51] Int. Cl.[4] .............................................. A61K 31/045
[52] U.S. Cl. ..................................... 514/729; 514/510; 514/532; 514/699
[58] Field of Search .......................................... 514/729

Primary Examiner—Stanley J. Friedman

[57] ABSTRACT

Polyene compounds represented by the formula

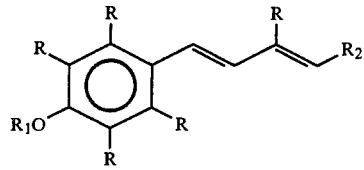

where
R is H or lower alkyl of from 1 to 5 carbon atoms;
$R_1$ is H, lower alkyl of from 1 to 8 carbon atoms or aralkyl; and
$R_2$ is $(CH_2)_n CH_2OH$, CHO or $CO_2R$; wherein n is 1 or 2.

The foregoing compounds have been found active in regulating the formation of lipoxygenase and as such possess therapeutic value in the treatment of inflammatory conditions and allergic responses.

2 Claims, No Drawings

POLYENE COMPOUNDS USEFUL IN THE TREATMENT OF ALLERGIC RESPONSES

BACKGROUND OF THE INVENTION

The present invention relates to polyene compounds and more particularly to dienoic compounds derived from aryl intermediates with the general formulae:

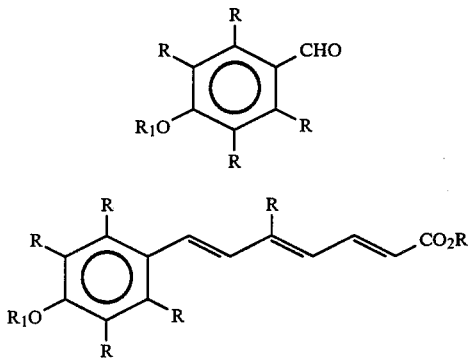

where

R is H or lower alkyl of from 1 to 5 carbon atoms $R_1$ is H, lower alkyl of from 1 to 8 carbon atoms or aralkyl.

A synthesis of methyl 7-(4-methoxy(-2,3,6-trimethylphenyl)-5-methyl-hepta-2,4,6-trienate is described in U.S. Pat. No. 4,534,979. A synthesis of 2,3,6-trimethyl-p-anisaldehyde is described in U.S. Pat. No. 4,105,681.

Other prior art publications include U.S. Pat. No. 4,137,246 and Swiss Pat. No. 616,134 describing the synthesis of certain pentadienals and esters of pentadienoic acids of the following formula as intermediates useful in the preparation of antitumour polyenoic agents:

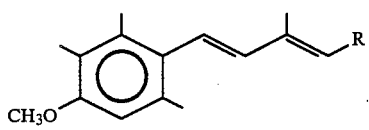

where

R is formyl and $CO_2CH_3$.

U.S. Pat. No. 4,534,979 describes the synthesis of 5-(2,3-dimethyl-4-methoxy-phenyl)-3-methyl-2,4-pentadien-1-al as intermediate for the preparation of antipsoriasis and anti-allergy polyenes. M. P. Reddy, et al. (*Synthesis*, 1980, (10), 815–18) describes the synthesis of some 5-aryl-3-methyl-2(E)-pentadienals and their oxidation to pentadienoic acids.

SUMMARY OF THE INVENTION

The present invention is directed to polyene compounds of the general formula

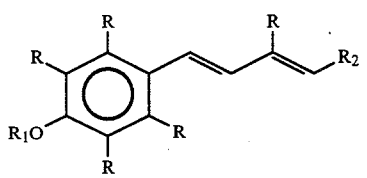

where

R is H or lower alkyl of from 1 to 5 carbon atoms;

$R_1$ is H, lower alkyl of from 1 to 8 carbon atoms or aralkyl; and $R_2$ is $(CH_2)_nCH_2OH$, CHO or $CO_2R$; wherein n is 1 or 2.

DETAILED DESCRIPTION OF THE INVENTION

The compounds of the formula I in which $R_2$ is $(CH_2)_n CH_2OH$ are prepared by reacting a compound of formula

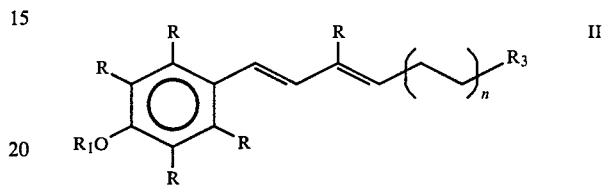

with a reducing agent, such as lithium aluminum hydride, in an organic solvent such as ethyl ether or tetrahydrofuran (THF);

wherein $R_3$ is CHO, OH or $CO_2R$; and R, $R_1$, and n are the same as described in formula I.

Compounds of formula I in which $R_2$ us $CO_2R$ are prepared by reacting compounds of formula

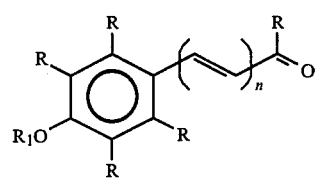

with a Horner reagents of formula

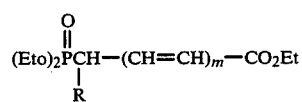

in the presence of sodium hydride or sodium amide in an organic solvent such as THF;

wherein the formulae III and IV, R, $R_1$, and n are the same as described in formula I, and in formula IV, m is 0–1.

The compounds of the formula I in which $R_2$ is CHO are prepared by reacting a compound of formula

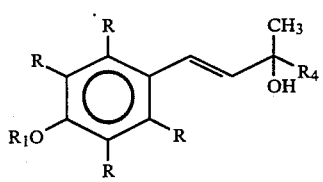

with Vilsmeier reagent ($POCl_3$/N,N-dimethylformamide), wherein in formula V, $R_4$ is H or methyl.

The preferred methods of synthesizing the compounds of the invention are described in the Examples that follow.

EXAMPLE 1

7-(4-Methoxy-2,3,6-trimethylphenyl)-5-methylhepta-4,6-diene-1-al

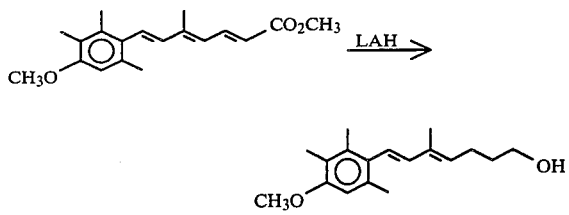

To a suspension of lithium aluminum hydride (400 mg) in 25 mL of diethyl ether stirred under nitrogen in an ice bath was added dropwise a solution of methyl 7-(4-methoxy-2,3,6-trimethylphenyl)-5-methylhepta-2,4,6-trienoate (2.1 g, 7 mmol) in 20 mL of diethyl ether and 5 mL of tetrahydrofuran. The mixture was stirred for 4½ hrs while its temperature was allowed to rise slowly to room temperature. Water (0.3 mL) was added dropwise to the mixture with stirring; a white precipitate occurred, which was removed by filtration. The filtrate was dried ($Na_2SO_4$) and concentrated in vacuo to give 2.2 g of pale yellow oil. This crude mixture was purified by a column chromatography (silica gel, 20% ethyl acetate in hexane) to afford 0.9 g of pure 7-(4-methoxy-2,3,6-trimethylphenyl)-5-methylhepta-4,6-diene-1-al as pale yellow oil. Crystallization from ethyl acetate/hexane gave white crystals: mp 42°–45° C.; MS (EI): 275 (m++1); NMR (COCl$_3$) δ5.40 (m. 3H), 6.00 (d,j=16 Hz,1H) 6.33 (d,j=16 Hz, 1H), 6.46 (s, 1H).

EXAMPLE 2

Ethyl 4-methoxy-2,3,6-trimethylcinnamate

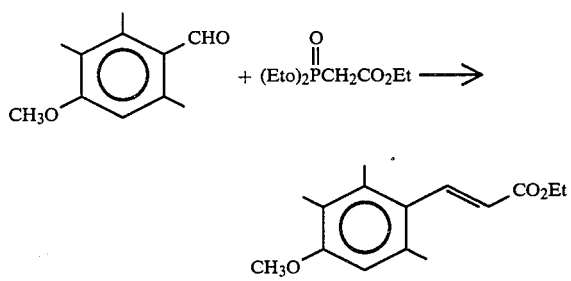

A suspension of NaH (9.3 g, 50% dispersion in oil, 0.19 mol) in 150 mL of tetrahydrofuran (THF) was stirred in an ice bath under an atmosphere of nitrogen and triethyl phosphonoacetate (43.5 g, 0.19 mol) was added dropwise within 15 min. The mixture was stirred for 1 hr in the ice bath and a solution of 2,3,6-trimethyl-p-anisaldehyde (24.3 g, 0.14 mol) in 100 mL of THF was added. The resulting mixture was stirred at room temperature for 18 hrs and brine (250 mL) and ethyl acetate (250 mL) was added. The layers were separated; the organic layer was washed with brine and dried (Na$_2$SO$_4$). Removal of solvent in vacuo afforded 32.3 g of yellow oil. A small portion of this product was recrystallized from ethyl ether to give white powders: mp 42°–44° C.; MS(CI): 249(m++1), 203. The rest of the product was used in the reaction described in Example 3 without further purification.

EXAMPLE 3

4-(4-Methoxy-2,3,6-trimethylphenyl)-2-methyl-3-buten-2-ol

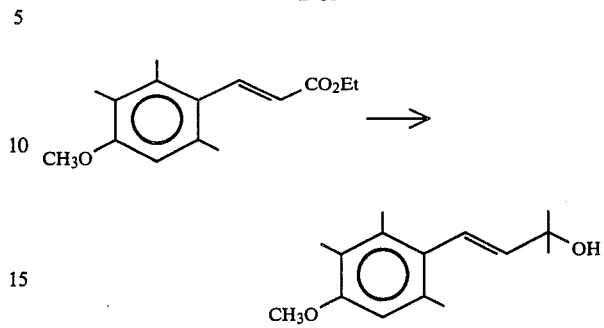

In a 3-necked, 250 mL round-bottomed flask, equipped with a nitrogen-inlet, a stopper and a low-temperature thermometer, was placed 28 mL of an ethereal solution of methyl magnesium bromide (2.9 molar solution, 0.08 mol). The stirred Grignard reagent was cooled to about −10° C. and a solution of ethyl 4-methoxy-2,3,6-trimethylcinnamate (4.9 g, 0.02 mol) in 35 mL of ethyl ether was added dropwise within 15 min. The resulting mixture was then stirred at room temperature for 18 hrs and heated to a gentle reflux for 2 hrs. The mixture was cooled in an ice bath and 15 mL of ice-cold water was added, followed by 5% aqueous NaHCO$_3$ solution. The mixture was extracted with ethyl ether; the combined ethereal solution was washed with brine and dried over Na$_2$SO$_4$. Removal of solvent in vacuo yielded a yellow oil, crystallization from ethyl ether-petroleum ether gave 3.64 g of white powders: mp 53°–57° C.

EXAMPLE 4

5-(4-Methoxy-2,3,6-trimethylphenyl)-3-methyl-2,4-pentadien-1-al

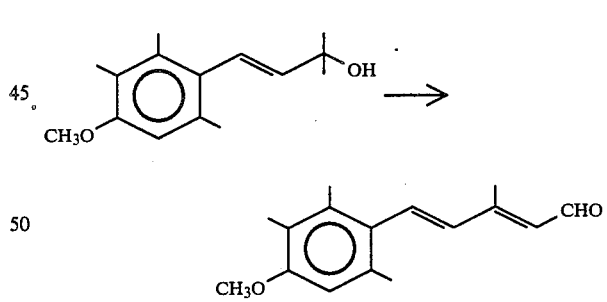

A solution of 4-(4-methoxy-2,3,6-trimethylphenyl)-2-methyl-3-buten-2-ol (3.98 g, 0.017 mol) in 8 mL of N,N-dimethylformamide (DMF) was stirred in an ice bath and the Vilsmeier reagent, which was prepared from 2.1 mL (3.4 g, 0.022 mol) of phosphoryl chloride and 3.5 mL of DMF at about 10° C., was added dropwise. The temperature of the reaction mixture was allowed to rise to 80° C. within 1 hr. The mixture was stirred for 3 hrs at 80° C. and, with cooling (ice bath), a solution of sodium acetate (10g) in 25 mL of water was added dropwise. The resulting mixture was heated to 80° C. for 10 min. After cooling to room temperature, the product was extracted into ethyl ether. Removal of solvent in vacuo afforded an orange-colored substance.

Crystallization from ethyl acetate-ethyl ether gave 2.2 g of the title compound as yellow crystals: mp 62°–64° C.

EXAMPLE 5

Ethyl 5-(2,3-Dimethyl-4-methoxyphenyl)-2,4-pentadienoate

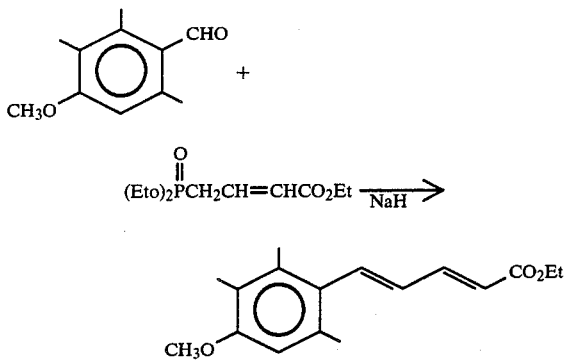

In a manner similar to Example 2, 16.5 g (0.1 mol) of 2,3-dimethyl-4-methoxybenzaldehyde was treated with triethyl phosphonocrotonate (30 g, 0.12 mol) in a modified Wittig reaction to give a yellow oil. Purification by a silica gel dry column (20% ethyl acetate in hexane) to give 12 g of the title compound as a yellow powder: mp 92°–95° C.

EXAMPLE 6

5-(2,3-Dimethyl-4-methoxyphenyl)-2,4-pentadienoic Acid

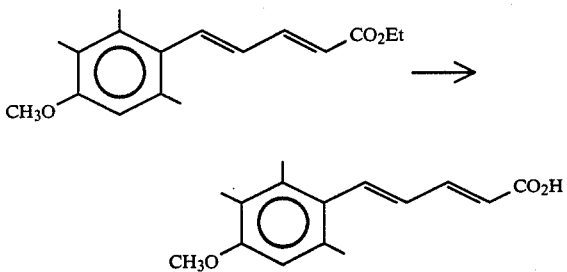

A solution of ethyl 5-(2,3-dimethyl-4-methoxyphenyl)-2,4-pentadienoate (2 g, 7.7 mmol) in 10 mL of ethanol was stirred at room temperature under nitrogen and a solution of KOH (1 g) in 2 mL of water was added dropwise. The mixture was stirred at room temperature for 18 hrs. and concentrated in vacuo. The residue was diluted with water and extracted several times with ethyl ether. The aqueous layer was acidified to pH 3 with a 10N HCl solution. The resulting yellow precipitate was extracted into ethyl acetate. The organic solution was washed with brine and dried ($Na_2SO_4$). Evaporation in vacuo afforded a yellow powder. Crystallization from ethyl acetate/ethyl ether gave 1.1 g of yellow crystals: MS (CI): 233 (M+1)+, 215.

Compounds of the present invention were found to have potent activity in regulating the formation of lipoxygenase and as such possess therapeutic value in the treatment of inflammatory conditions and allergic responses such as anaphylaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygenases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 4,12-diHETE are chemotactic for human neutrophils and eosinophils, and may augment the inflammation process, 5-HPETE is known to be a precursor of slow-reacting substance of anaphylaxis (SRS-A). The SRS family of molecules, such leukotrienes B, C, and D, have been shown to be potent bronchoconstrictors (see, NATURE 288, 484–486 (1980)).

Protocol I describes an assay to detect inhibitors of the lipoxygenase pathway. Such inhibitors are believed to be capable of modulating the biosynthesis of the leukotrienes, a property believed to be useful in treating asthma and inflammatory disease states.

PROTOCOL I

A suspension of rat neutrophils in buffer is incubated for 3 minutes at 30° C. with [$^{14}$C]-arachidonic acid (AA) and Calcium Ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spoted on silica gel TLC sheets, which are developed with an ethyl acetate/isooctane/water acetic acid solvent system. The 5-HETE spots are visulaized with iodine, cut out and placed in scintillation vials for counting. After adjusting for the extraction efficiency, the amount (pmole) of [$^{14}$C]-5-HETE in each of the tubes is quantitated. The net pmoles of 5-HETE are obtained by subtracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

The concentration required for inhibition of the 5-lipoxygenase pathway (5-Lox/$I_{50}$ $\mu$M) for the compound of the Example 1 is 11 $\mu$M.

(Standard used: all-trans retinoic acid: 90 $\mu$M
  Ro 10-9359: 10±17% I at 50 $\mu$M
  Ro 11-1430: 11±19% I at 50 $\mu$M)

PROTOCOL II

In Vitro Assay For Inhibitors of Phospholipase $A_2$ Assayed at pH 7.0 ($PLA_2$)

The $PLA_2$ employed in this screen is obtained by aggregation of purified rat platelets. In the enzyme assay phosphatidylcholine having $^{14}$C-labeled palmitate residues at $R_1$ and $R_2$ is employed as substrate. $PLA_2$ acts by cleaving the $R_2$ fatty acid ester bond yielding free fatty acid and lysophosphatidylcholine as follows:

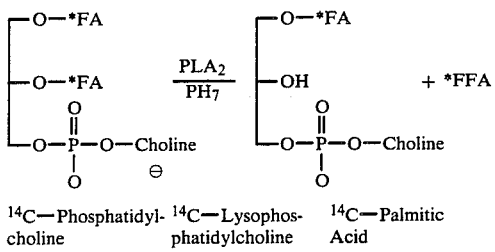

$^{14}C$—Phosphatidylcholine  $^{14}C$—Lysophosphatidylcholine  $^{14}C$—Palmitic Acid Following completion of the reaction, the assay medium is acidified and extracted with hexane, which takes up unreacted substrate and free fatty acid product. The hexane extract is passed over a short silica column which retains 99% of the phosphatidylcholine. The $^{14}C$-labeled palmitic acid is not retained (90% recovery in eluate) and is collected directly in scintillation counting vials. The released palmitic acid is conveniently quantitated by liquid scintillation spectrometry.

The compounds were tested at 100 μM in a buffer containing 0.3 mM unlabeled phosphatidylcholine (PC), 20–30,000 cpm of $^{14}C$(CPC), 100 μM NaCl, 1 mM CaCl$_2$ and 50 mM tris-HCl adjusted to pH 7.2 with 1N NaOH. This resulted in a buffer at pH 7.2. The temperature of the buffer was maintained at a temperature of 37° C. The reaction was initiated by addition of the enzyme and it was terminated 30 minutes later by the addition of 100 ml of 1N HCl.

Following acidification, the samples were extracted with 2 ml of 2-propanol and 2 ml of hexane, vortexed and allowed to stand until the phases separated. Free fatty acids (FFA) and some unreacted substrate were taken up in the isopropanol-saturated hexane. The hexane phase of the extraction mixture was transferred to a short silica gell column which retained reacted PC but not the FFA. The column effluent was collected directly in scintillation vials. The columns were washed once with an additional 2 ml of hexane. The radio labeled FFA were quantitated by liquid scintillation spectrometry.

The compound of the Example 1 showed a phospholipase A$_2$ inhibition activity of 58 μM at I$_{50}$ (Standard used: all-trans retinoic acid: 32% I at 100 μM)

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk, sugar, certain types of clay and so forth. They may be administered orally in the form of solutions which may contain coloring and flavoring agents or they may be injected parenterally, that is intramuscularly, intravenously or subcutaneously. For parenteral administration, they may be used in the form of a sterile solution containing other solutes, for example, enough saline or glucose to make the solution isotonic. When applied topically for treating skin disorders, the present new products can be provided in the form of dusting powders, aerosol sprays, ointments, aqueous compositions including solutions and suspensions, cream lotions and the like. In this regard, any of the commonly employed extending agents can be used depending on the nature of the product as is well-known in the art.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally.

What is claimed is

1. A therapeutic composition for the treatment of inflammatory conditions and allergic responses in a human host, in combination with at least one pharmaceutically acceptable extender, a therapeutically effective amount of a compound of the formula

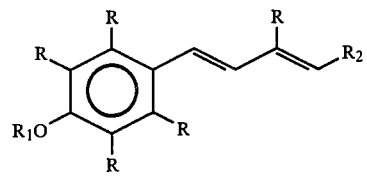

where
R is H or lower alkyl of from 1 to 5 carbon atoms;
R$_1$ is H, lower alkyl of from 1 to 8 carbon atoms or aralkyl; and
R$_2$ is (CH$_2$)$_n$CH$_2$OH; wherein n is 1 or 2.

2. A method for treating inflammatory conditions and allergic responses in a human host which comprises administering to said host a therapeutically effective amount of at least one compound of the formula

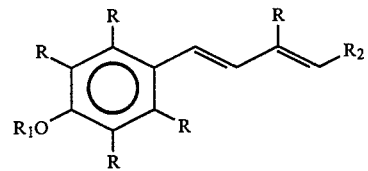

where
R is H or lower alkyl of from 1 to 5 carbon atoms;
R$_1$ is H, lower alkyl of from 1 to 8 carbon atoms or aralkyl; and
R$_2$ is (CH$_2$)$_n$CH$_2$OH; wherein n is 1 or 2.

* * * * *